United States Patent
Le et al.

(10) Patent No.: US 10,299,798 B2
(45) Date of Patent: May 28, 2019

(54) PACKING COIL

(75) Inventors: Jake Le, Lake Forest, CA (US); Heath Bowman, Trabuco Canyon, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 949 days.

(21) Appl. No.: 13/470,127

(22) Filed: May 11, 2012

(65) Prior Publication Data

US 2013/0018409 A1    Jan. 17, 2013

Related U.S. Application Data

(60) Provisional application No. 61/485,059, filed on May 11, 2011, provisional application No. 61/536,478, filed on Sep. 19, 2011.

(51) Int. Cl.
*A61M 29/00* (2006.01)
*A61B 17/12* (2006.01)
*A61B 17/00* (2006.01)
*A61B 17/42* (2006.01)

(52) U.S. Cl.
CPC .. *A61B 17/12145* (2013.01); *A61B 17/12109* (2013.01); *A61B 17/12113* (2013.01); *A61B 17/12122* (2013.01); *A61B 17/12172* (2013.01); *A61B 2017/00526* (2013.01); *A61B 2017/00592* (2013.01); *A61B 2017/00867* (2013.01); *A61B 2017/4233* (2013.01)

(58) Field of Classification Search
CPC .......... A61B 17/1214; A61B 17/12145; A61B 17/12172; A61B 2017/00526; A61B 17/12109; A61B 17/12113; A61B 17/12122; A61F 6/20; A61F 6/142
See application file for complete search history.

(56) References Cited

U.S. PATENT DOCUMENTS

| | | | |
|---|---|---|---|
| 5,639,277 A | | 6/1997 | Mariant et al. |
| 5,911,731 A | * | 6/1999 | Pham ............... A61B 17/12022 140/92.1 |
| 5,980,554 A | * | 11/1999 | Lenker ............. A61B 17/12022 606/198 |
| 6,183,495 B1 | | 2/2001 | Lenker et al. |
| 6,860,893 B2 | | 3/2005 | Wallace et al. |
| 7,070,608 B2 | | 7/2006 | Kurz et al. |

(Continued)

FOREIGN PATENT DOCUMENTS

| | | |
|---|---|---|
| JP | 2001513389 A | 9/2001 |
| JP | 2002523125 A | 7/2002 |

(Continued)

OTHER PUBLICATIONS

WIPO, U.S. International Search Authority, International Search Report and Written Opinion dated Aug. 23, 2012 in International Patent Application No. PCT/US2012/037633, 7 pages.

(Continued)

*Primary Examiner* — Elizabeth Houston
*Assistant Examiner* — Kankindi Rwego
(74) *Attorney, Agent, or Firm* — Inskeep IP Group, Inc.

(57) ABSTRACT

An occlusion device formed of a microcoil having a three-dimensional relaxed state employing open looped portions interposed between closed loop portions. Planes defined by sequentially formed open looped and closed loop portions are neither coincident nor parallel to one another.

15 Claims, 14 Drawing Sheets

(56) References Cited

U.S. PATENT DOCUMENTS

| | | | |
|---|---|---|---|
| 7,488,332 B2* | 2/2009 | Teoh | A61B 17/12022 606/113 |
| 8,323,306 B2 | 12/2012 | Schaefer et al. | |
| 2006/0184195 A1 | 8/2006 | Schaefer et al. | |
| 2006/0217760 A1 | 9/2006 | Widomski et al. | |
| 2007/0175536 A1 | 8/2007 | Monetti et al. | |
| 2009/0149864 A1* | 6/2009 | Porter | 606/113 |
| 2009/0297582 A1 | 12/2009 | Meyer et al. | |
| 2010/0234872 A1* | 9/2010 | Guo | A61B 17/12022 606/191 |
| 2011/0098814 A1 | 4/2011 | Monstadt et al. | |

FOREIGN PATENT DOCUMENTS

| | | |
|---|---|---|
| JP | 2006500108 A | 1/2006 |
| JP | 2007525304 A | 9/2007 |
| JP | 2009516547 A | 4/2009 |
| WO | WO1999009893 A1 | 3/1999 |
| WO | WO2000010469 A1 | 3/2000 |
| WO | WO2004026149 A1 | 4/2004 |
| WO | WO2005092213 A1 | 10/2005 |
| WO | WO2007076179 A2 | 7/2007 |

OTHER PUBLICATIONS

IP Australia, Notice of Acceptance dated Nov. 10, 2016 in Australian Patent Application No. AU2012253287, 2 pages.

Japan Patent Office, Final Official Action dated Nov. 1, 2016 in Japanese Patent Application No. JP2014-510516 with English translation, 5 pages.

State Intellectual Property Office, P.R. China, Notification to Grant Patent Right for Invention dated Jul. 5, 2016 in Chinese Patent Application No. CN201280034293.4 with English translation, 4 pages.

IP Australia, Examination Report No. 2 dated Jun. 23, 2016 in Australian Patent Application No. AU2012253287, 4 pages.

Japan Patent Office, Official Action dated Feb. 26, 2016 in Japanese Patent Application No. JP2014-510516 with English translation, 7 pages.

IP Australia, Examination Report No. 1 dated Nov. 26, 2015 in Australian Patent Application No. AU2012253287, 3 pages.

State Intellectual Property Office, P.R. China, Second Office Action dated Oct. 23, 2015 with English translation in Chinese Patent Application No. CN201280034293.4, 20 pages.

State Intellectual Property Office, P.R. China, First Office Action dated Apr. 3, 2015 with English translation in Chinese Patent Application No. CN201280034293.4, 20 pages.

European Patent Office, Extended European Search Report dated Feb. 4, 2014 in European Patent Application No. EP12782929.9-1654, 5 pages.

WIPO, U.S. International Search Authority, International Search Report and Written Opinion dated Aug. 23, 2012 in International Patent Application No. PCT/US2012/037633, 15 pages.

* cited by examiner

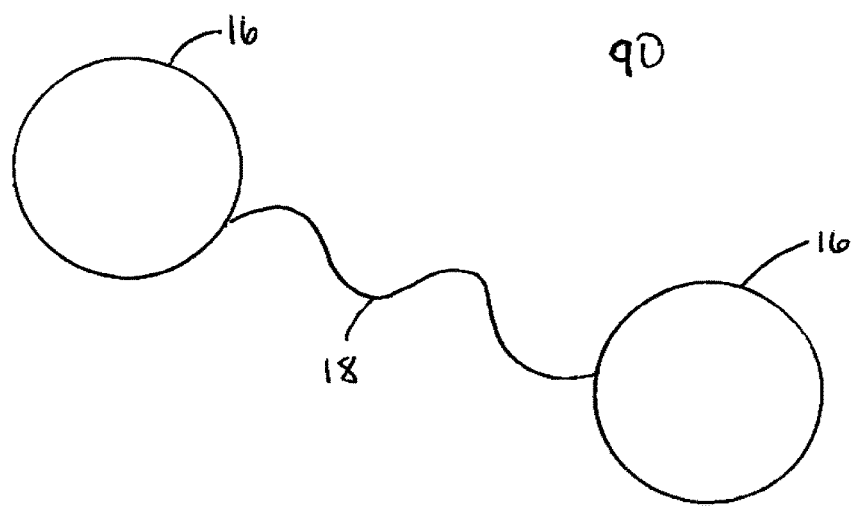

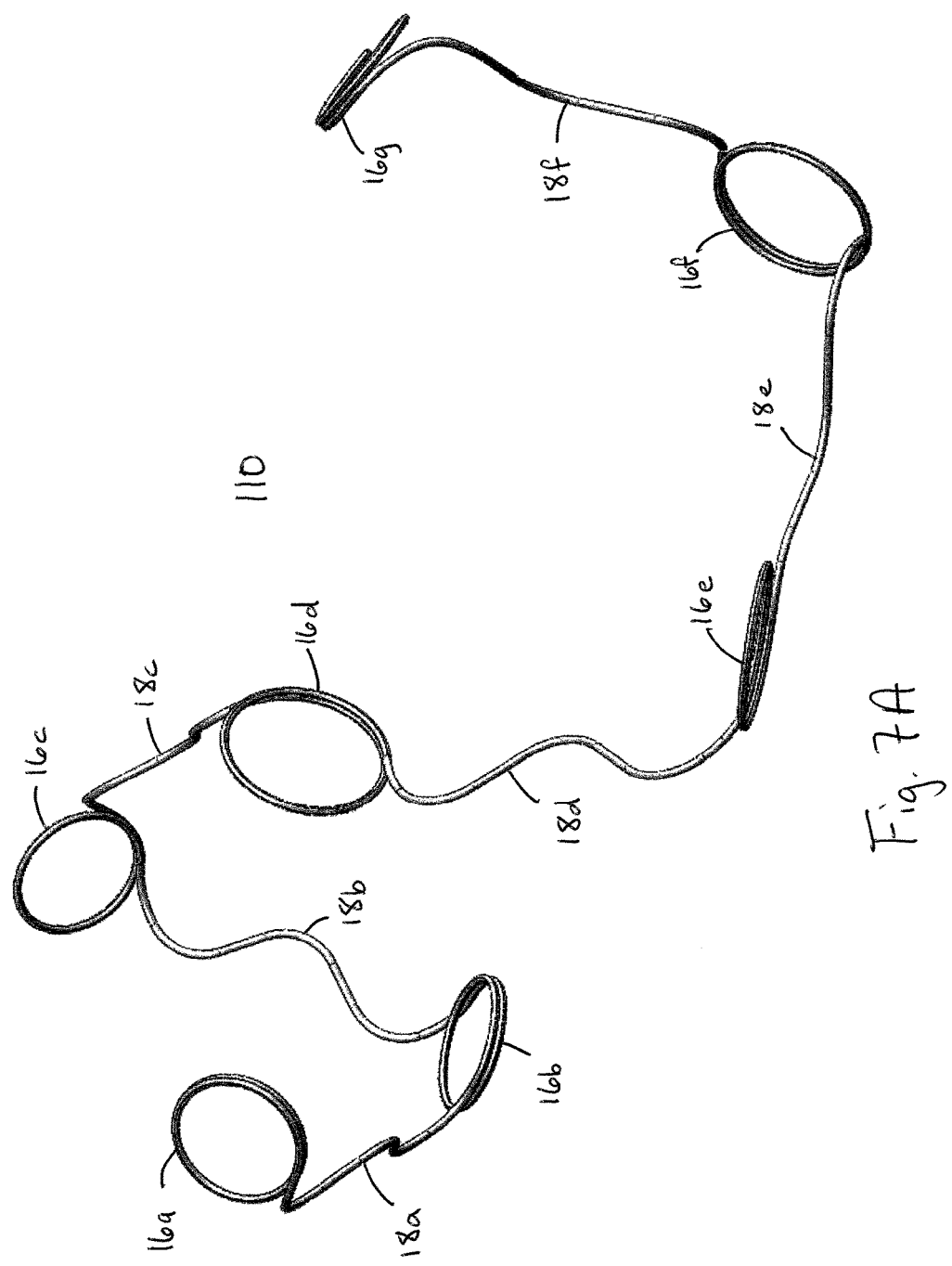

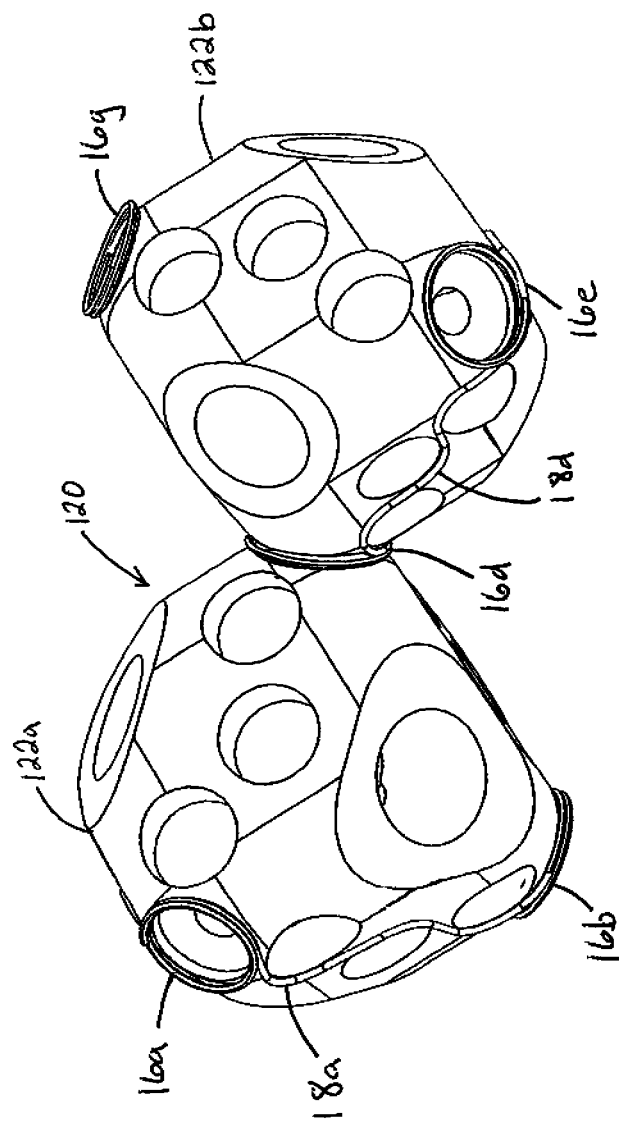

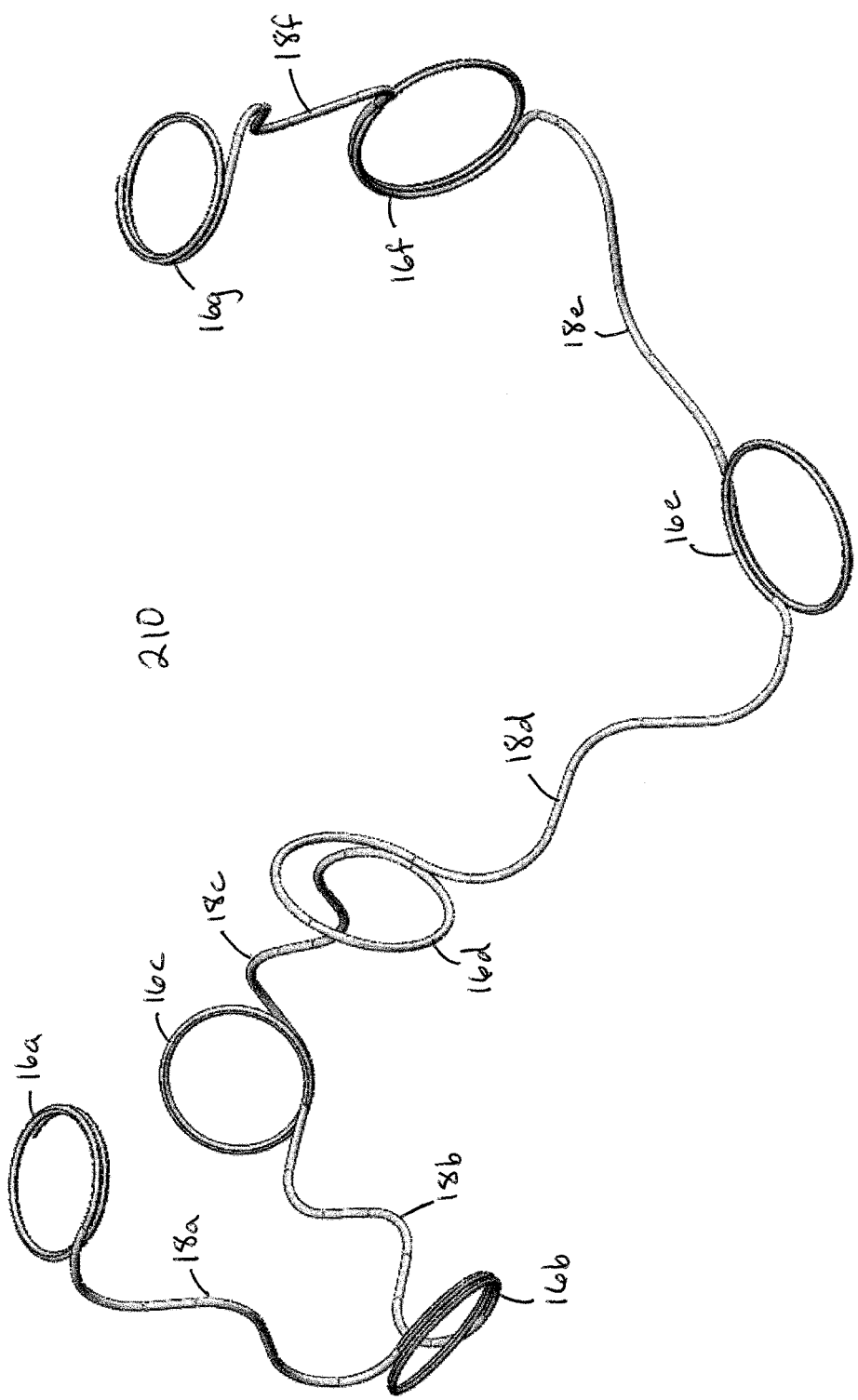

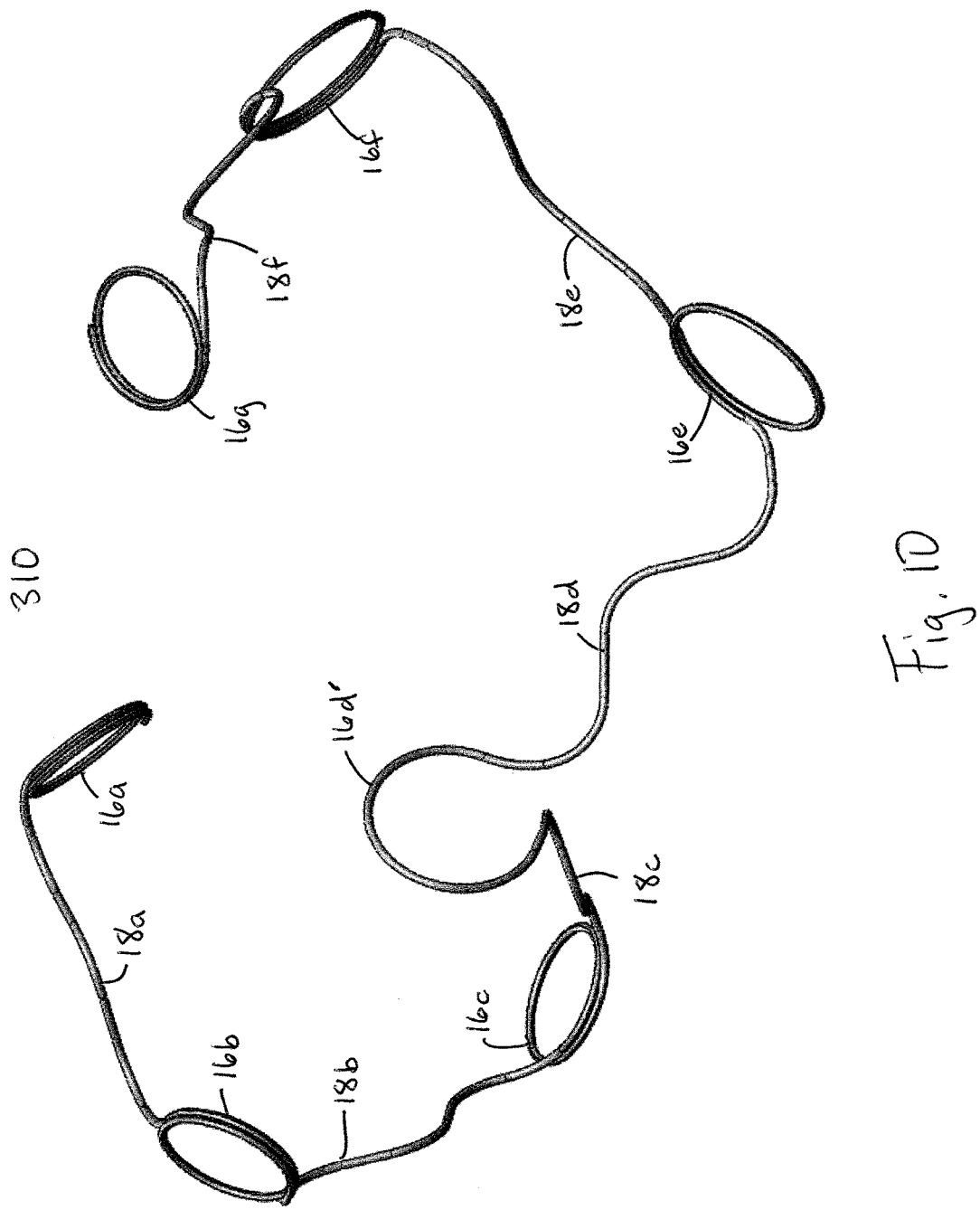

TABLE 1

| Diameter of Closed Loop Portions 16 | Rotations Forming Closed Loop Portion 16 | Rotations Forming Closed Loop Portion 16b | Rotations Forming Closed Loop Portion 16c | Rotations Forming Closed Loop Portion 16d | Rotations Forming Closed Loop Portion 16e | Rotations Forming Closed Loop Portion 16f | Rotations Forming Closed Loop Portion 16g | No. of Open Loop Portions 18 |
|---|---|---|---|---|---|---|---|---|
| 3 mm | 1.5 | 1.5 | 2 | 1 | NA | NA | NA | 3 |
| 3 mm | 1.5 | 1.5 | 2.25 | 1 | 1.5 | NA | NA | 4 |
| 3 mm | 1.5 | 1.5 | 2.25 | 1 | 2.25 | 1.5 | 2 | 6 |
| 6 mm | 1.5 | 1.5 | 2.25 | 1 | 1.5 | NA | NA | 4 |
| 6 mm | 1.5 | 1.5 | 2.25 | 1 | 2.25 | 1.5 | 2 | 6 |
| 10 mm | 1.5 | 1.5 | 2.25 | 1 | NA | NA | NA | 3 |
| 10 mm | 1.5 | 1.5 | 2.25 | 1 | 2 | NA | NA | 4 |
| 15 mm | 1.5 | 1.5 | 1.25 | 1 | NA | NA | NA | 3 |
| 15 mm | 1.5 | 1.5 | 2.25 | 1 | 2 | NA | NA | 4 |

FIG. 11

PACKING COIL

RELATED APPLICATIONS

This application claims priority to U.S. Provisional Application Ser. No. 61/485,059 filed May 11, 2011 entitled Packing Coil, and to U.S. Provisional Application Ser. No. 61/536,478 filed Sep. 19, 2011 entitled Packing Coil, both of which are hereby incorporated herein by reference in their entireties.

FIELD OF THE INVENTION

The present invention relates to devices for the occlusion of body cavities, such as the embolization of vascular aneurysms and the like, and methods for making and using such devices.

BACKGROUND OF THE INVENTION

The occlusion of body cavities, blood vessels, and other lumina by embolization is desired in a number of clinical situations. For example, the occlusion of fallopian tubes for the purposes of sterilization, and the occlusive repair of cardiac defects, such as a patent foramen ovale, patent ductus arteriosis, and left atrial appendage, and atrial septal defects. The function of an occlusion device in such situations is to substantially block or inhibit the flow of bodily fluids into or through the cavity, lumen, vessel, space, or defect for the therapeutic benefit of the patient.

The embolization of blood vessels is also desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been shown in the prior art. One approach that has shown promise is the use of thrombogenic microcoils. These microcoils may be made of biocompatible metal alloy(s) (typically a radio-opaque material such as platinum or tungsten) or a suitable polymer. Examples of microcoils are disclosed in the following patents: U.S. Pat. No. 4,994,069 to Ritchart et al.; U.S. Pat. No. 5,133,731 to Butler et al.; U.S. Pat. No. 5,226,911 to Ghee et al.; U.S. Pat. No. 5,312,415 to Palermo; U.S. Pat. No. 5,382,259 to Phelps et al.; U.S. Pat. No. 5,382,260 to Dormandy, Jr. et al.; U.S. Pat. No. 5,476,472 to Dormandy, Jr. et al.; U.S. Pat. No. 5,578,074 to Mirigian; U.S. Pat. No. 5,582,619 to Ken; U.S. Pat. No. 5,624,461 to Mariant; U.S. Pat. No. 5,645,558 to Horton; U.S. Pat. No. 5,658,308 to Snyder; and U.S. Pat. No. 5,718,711 to Berenstein et al.; all of which are hereby incorporated by reference.

A specific type of microcoil that has achieved a measure of success is the Guglielmi Detachable Coil ("GDC"), described in U.S. Pat. No. 5,122,136 to Guglielmi et al. The GDC employs a platinum wire coil fixed to a stainless steel delivery wire by a solder connection. After the coil is placed inside an aneurysm, an electrical current is applied to the delivery wire, which electrolytically disintegrates the solder junction, thereby detaching the coil from the delivery wire. The application of current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

Alternative vaso-occlusive devices are exemplified in U.S. Pat. No. 6,299,619 to Greene, Jr. et al.; U.S. Pat. No. 6,602,261 to Greene, Jr. et al.; U.S. Pat. No. 6,605,101 to Schafer et al.; U.S. Pat. No. 7,029,486 to Schaefer et al.; U.S. Pat. No. 7,033,374 to Schaefer et al.; U.S. Pat. No. 7,331,974 to Schaefer et al.; and in co-pending U.S. patent application Ser. No. 10/631,981 to Martinez; U.S. patent application Ser. No. 11/398,081 to Schaefer et al.; and U.S. patent application Ser. No. 11/398,082 to Schaefer et al., all of which are assigned to the assignee of the subject invention and incorporated herein by reference.

There is, however, an ongoing need to provide more advanced and improved neuro-embolic microcoils that exhibit greater stability after deployment in a target site; improved space seeking ability within the target site; wider application for treatment of target sites of varying sizes; and increased efficacy for treating and occluding the target site.

OBJECTS AND SUMMARY OF THE INVENTION

The present invention provides a more advanced and improved occlusion device, for example an occlusion device in the form of a neuro-embolic microcoil, that exhibits greater stability after deployment in a target site; improved space seeking ability within the target site; wider application for treatment of target sites of varying sizes; and increased efficacy for treating and occluding the target site. In one embodiment, the occlusion device comprises a microcoil having a relaxed configuration comprising a plurality of open loop portions interposed between a plurality of closed loop portions.

In another embodiment, the occlusion device comprises a microcoil having a relaxed configuration comprising a plurality of open loop portions interposed between a plurality of closed loop portions, each of the plurality of open looped portions formed substantially within a different plane.

In another embodiment, the present invention provides a method for occluding a body cavity comprising passing a delivery system through a vasculature until a distal end of the delivery system is positioned at a target location; advancing a first portion of the occlusion device from the distal end of the delivery system into the target site, the first portion forming a closed loop when the occlusion device is in a relaxed state; advancing a second portion of the occlusion device from the distal end of the delivery system into the target site, the second portion forming at least one open loop when the occlusion device is in a relaxed state; advancing a third portion of the occlusion device from the distal end of the delivery system into the target site, the first portion forming a closed loop when the occlusion device is in a relaxed state; and releasing the occlusion device from the delivery system and withdrawing the delivery system from the vasculature.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 6 is a perspective view of a device according to one embodiment of the present invention.

FIG. 7A is a perspective view of a device according to one embodiment of the present invention.

FIG. 7C is a perspective view of a device on a mandrel according to one embodiment of the present invention.

FIG. 9 is a perspective view of a device according to one embodiment of the present invention.

FIG. 10 is a perspective view of a device according to one embodiment of the present invention.

FIG. 11 is a table describing various configurations of a device according to one embodiment of the present invention.

DESCRIPTION OF EMBODIMENTS

Figure 1:
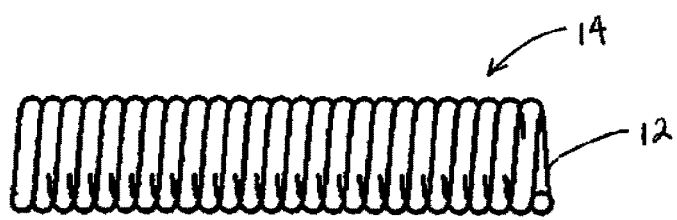
FIG. 1 is a perspective view of a portion of a microcoil employed to form a device according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Devices or packing coils according to the present invention provide improved stability after deployment in a target site; improved space seeking ability within the target site; wider application for treatment of target sites of varying sizes; and increased efficacy for occlusion and treatment of the target site. Broadly speaking, these objectives are achieved by employing a microcoil having a relaxed, low-energy state configuration incorporating both closed loop portions and open loop portions.

With reference to FIG. 1, devices or packing coils according to the present invention are formed of a suitable length of wire 12 formed into a primary winding in the shape of a helical microcoil 14. Suitable materials for the wire 12 include platinum, rhodium, palladium, rhenium, tungsten, gold, silver, tantalum, and various alloys of these metals. Various surgical grade stainless steels may also be used. Preferred materials include the platinum/tungsten alloy known as Platinum 479 (92% Pt, 8% W, available from Sigmund Cohn, of Mount Vernon, N.Y.) and titanium/nickel alloys (such as the titanium/nickel alloy known as "Nitinol"). Another material that may be advantageous is a bimetallic wire comprising a highly elastic metal with a highly radiopaque metal. Such a bimetallic wire would also be resistant to permanent deformation. An example of such a bimetallic wire is a product comprising a Nitinol outer layer and an inner core of pure reference grade platinum, available from Sigmund Cohn, of Mount Vernon, N.Y., and Anomet Products, of Shrewsbury, Mass.

In embodiments useful for treating neurovascular malformations, the wire 12 employed to form microcoil 14 has, for example, a diameter in the range of 0.001 to 0.005 inches. The microcoil 14 has a diameter that is in the range of about 0.008 to 0.016 inches. The axial length of the microcoil 14 may be anywhere from about 2 to 100 cm. In embodiments useful for treating larger malformations that may occur in the peripheral vasculature, the wire 12 may be larger, for example from 0.005 to 0.015 inches. The microcoil 14 may have a diameter in the range of about 0.010 to 0.050 inches. The axial length of the microcoil may be from 1 to 200 cm. Those skilled in the art will appreciate that the wire size, coil diameter, and length are a matter of design selection and are usually scaled to the malformation intended to be treated.

The primary winding of the microcoil 14 is applied under tension. The amount of tension and the pitch of the primary winding determine the stiffness of the microcoil 14. These parameters can be varied along the length of the microcoil 14 to form a microcoil having different degrees of stiffness along its length, which may be advantageous in certain applications.

The microcoil 14 is formed into a relaxed or minimum energy state configuration by winding or otherwise manipulating the microcoil 14 about a fixture or mandrel 20. Once associated with the mandrel 20, the microcoil 14 and the mandrel 20 are subjected to a heat treatment, as is well known in the art. For example, an annealing temperature of about 500 degrees Celsius to about 1000 degrees Celsius is maintained for about 30 to 90 minutes, the microcoil 14 and the mandrel 20 are then cooled to room temperature and ultrasonically cleaned. The resultant secondary configuration is thereby made permanent and becomes the relaxed or minimum energy state configuration of the device 10.

Figure 2:
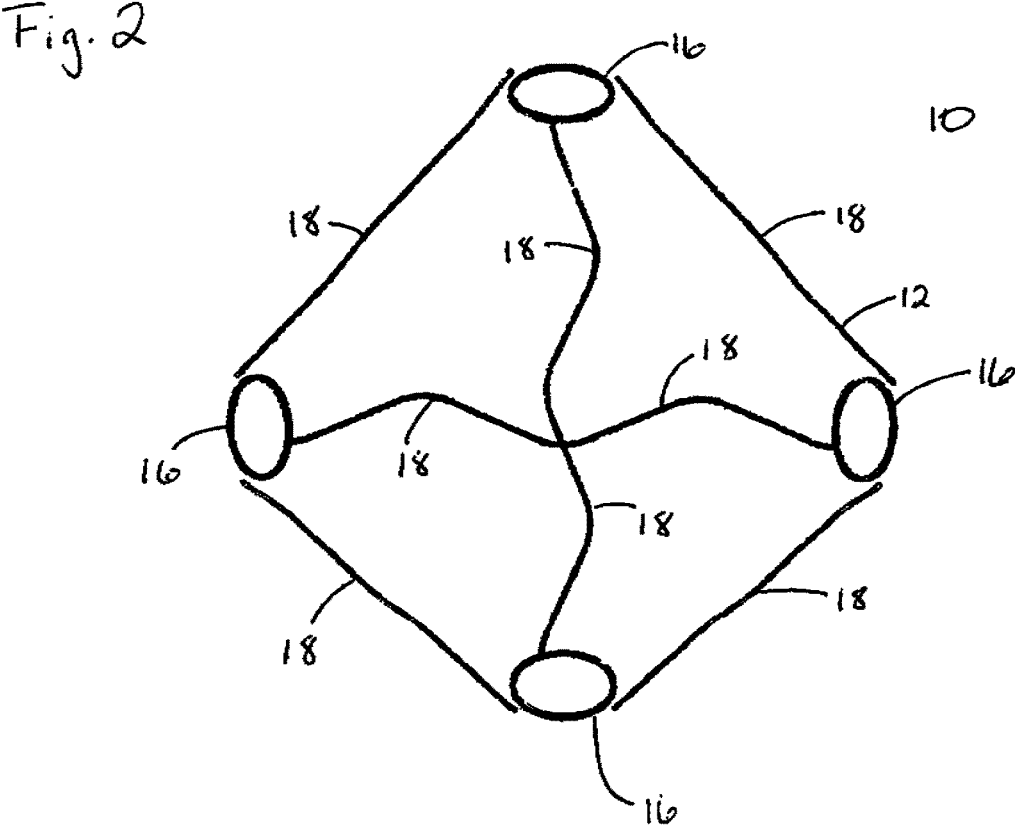
FIG. 2 is a perspective view of device according to one embodiment of the present invention.

With reference to FIG. 2, a device or packing coil 10 according to one embodiment of the present invention employs a closed loop portion 16 and an open loop portion 18. The closed loop portions 16 form substantially closed loops. The term "closed loop" refers to the feature in which a portion of the microcoil 14 approximately returns to or contacts another portion of the same microcoil 14. Such a return or contact may, for example, appear as a stacking of two portions of the microcoil 14 on top of one another, as shown in FIGS. 7A, 8A, 9, and 10. The substantially closed loops formed by the closed loop portion 16 may be formed in the general shape of circles, ovals or other regular geometric or irregular shapes and need not be uniformly formed within the same device 10.

Figure 3:
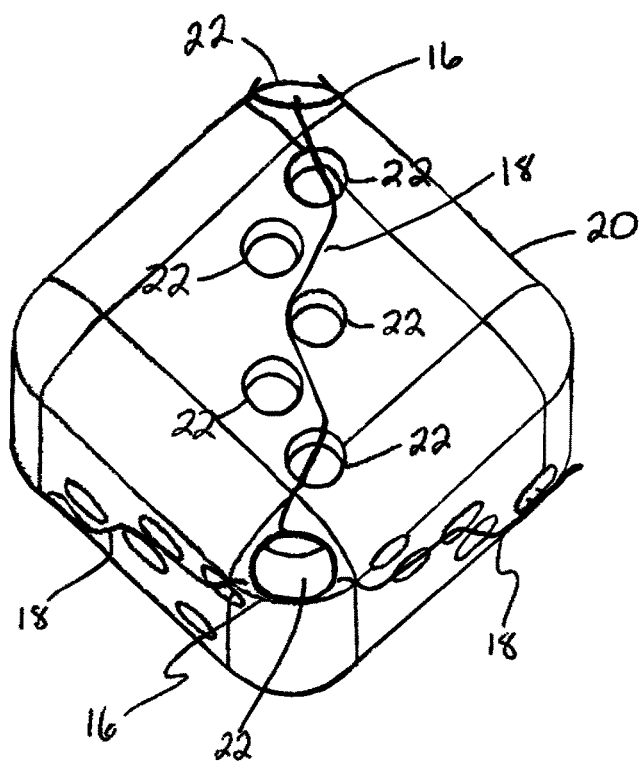
FIG. 3 is a perspective view of a device on a mandrel employed to fabricate the device according to one embodiment of the present invention.
Figure 4:
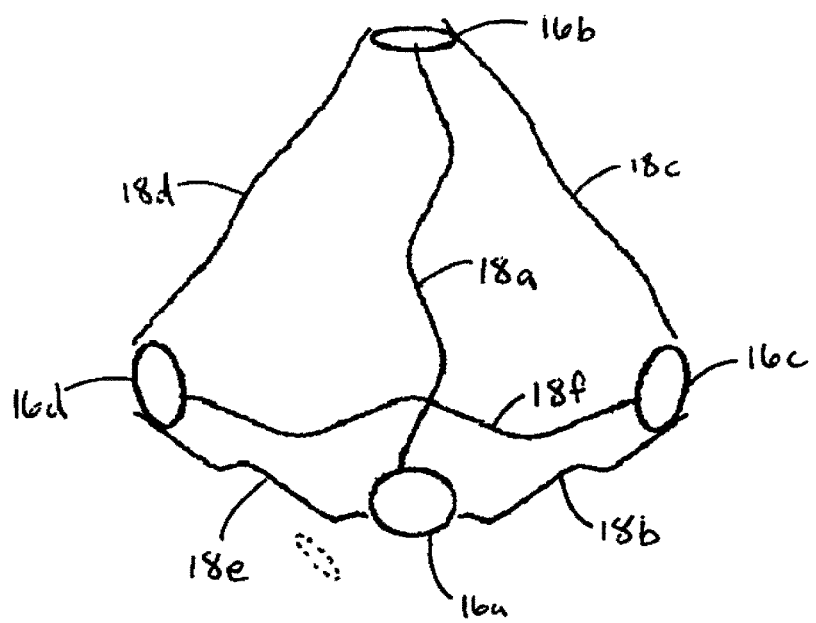
FIG. 4 is a perspective view of a device according to one embodiment of the present invention.

As shown in FIGS. 2-4, some or all of the closed loop portions 16 may define a plane. That is to say, the closed loop portions 16 may be substantially flat and define an area or boundary through which a plane could be approximately positioned. It is further contemplated that some or all of the closed loop portions 16 may define one or more curves in the X and the Y planes. Furthermore, some or all of the closed loop portions 16 have diameters of equal lengths. In one embodiment, at least one of the diameters of the closed loop portions 16 is formed relative to a dimension of a vascular site in which the device 10 is intended to be placed. In certain embodiments of the present invention, the closed loop portions 16 have diameters of different lengths such as that shown in FIG. 10. For example, the diameter of the closed loop portions 16 may sequentially increase, decrease, alternate between increasing and decreasing, or otherwise vary throughout the coil 10.

The closed loop portions 16 are, for example, formed by winding the microcoil 14 around pins 22 that project outward from the mandrel 20 one or more rotations. For example, the closed loop portions 16 may be formed by winding the microcoil 14 around the pin 22 in the range of 1 to 4 rotations. The closed loop portions 16 may be wound about the pins 22 in either a clockwise or a counterclockwise direction. The direction of the windings may but need not be uniform throughout the device 10. The direction of the windings about the pins 22 of the present invention may be determined from the perspective of viewing down the length of the pin 22 with the free end of the pin 22 closest to the viewer. Where the microcoil 14 is stacked upon itself, the portion of the winding furthest from the viewer, i.e. on the bottom of the stack, represents the beginning of the winding and the portion closest to the viewer represents a subsequent or later portion of the winding. Stated alternatively, a winding or loop is formed from the bottom up relative to the mandrel 20.

The open loop portions 18 of the device 10 are formed in the shape of a series of open loops, curves, or waves spanning, for example as shown in FIGS. 2-4, between two closed loop portions 16. The term "open loop" refers to the feature in which a portion of the microcoil 14 folds or doubles on to itself without contacting itself, thereby leave an opening. The individual open loops of the open loop portion 18 may, for example, have a "C", "U", or "V" like form. It is noted that the individual open loops of the open looped portions 18 may be formed by winding the microcoil 14 around a portion of the pin 22 less than one full rotation. For example, a single open loop portion 18 may employ three individual open loops each formed by winding the microcoil 14 about a portion of a different pin 22 and each separated from one another by an inflection point. A single open looped portion 18 may employ between one and 10 individual open loops.

Figure 12:
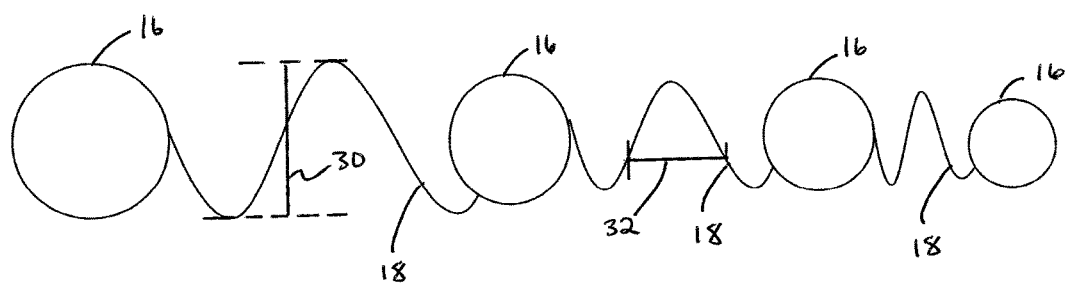
FIG. 12 is a perspective view of a device according to one embodiment of the present invention.

The form or shape of the individual open loops within a single open loop portion 18 may be the same or vary. The number and the form of the individual open loops employed within different open loop portions 18 may be the same or vary between different open loop portions 18 within a single device 10. As shown in FIG. 12, the height 30 of individual open loops relative to one another, for example determined as the distance between sequentially formed curves of the individual open loops, may be the same or vary within a single open loop portion 18 and may be the same or vary between different open loop portions 18 within a single device 10. As also shown in FIG. 12, the width 32 of individual open loops relative to one another, for example determined as the distance between the inflection points of sequentially formed individual open loops, may be the same or vary within a single open loop portion 18 and may be the same or vary between different open loop portions 18 within a single device 10.

As shown in FIGS. 2-5C 7A, 7C, 8A, 8C, 9, and 10, the open loop portions 18 may be formed substantially within a single plane, i.e. the open loop portions 18 may be substantially flat. Alternatively, the open loop portions 18 may be formed substantially within one or more curves in the X and Y planes.

In one embodiment of the present invention, the relaxed or minimum energy state configuration of the device 10 may be formed on a mandrel 20, for example, having a generally cube-like shape, as shown in FIGS. 3, and 5A-5C. FIGS. 2 and 4 show one example of a device 10 formed on such a cube-like mandrel 20.

Figure 5A:
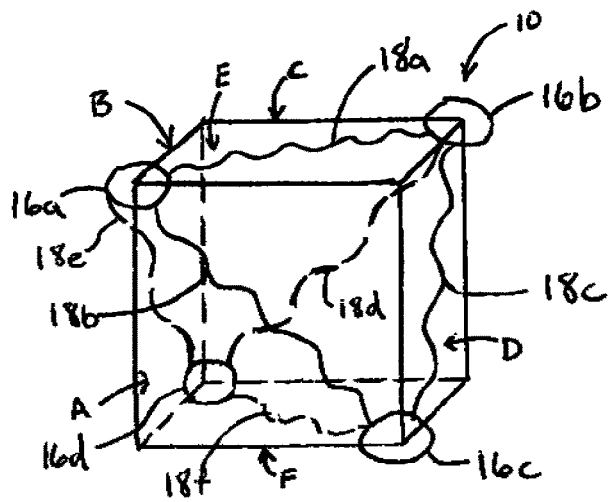
FIGS. 5A through 5C are perspective views of a device on a mandrel employed to fabricate the device according to one embodiment of the present invention.
Figure 5B:
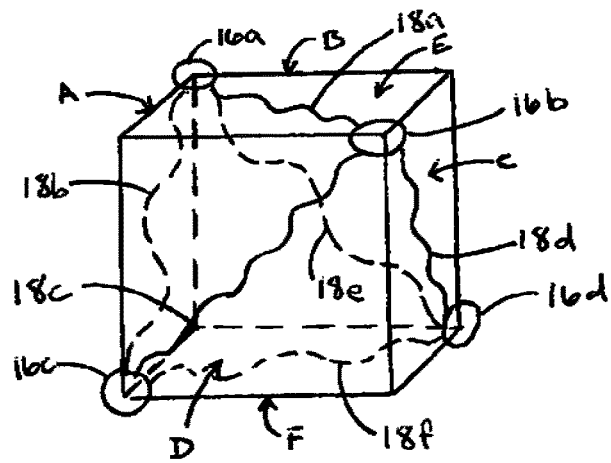
Figure 5C:
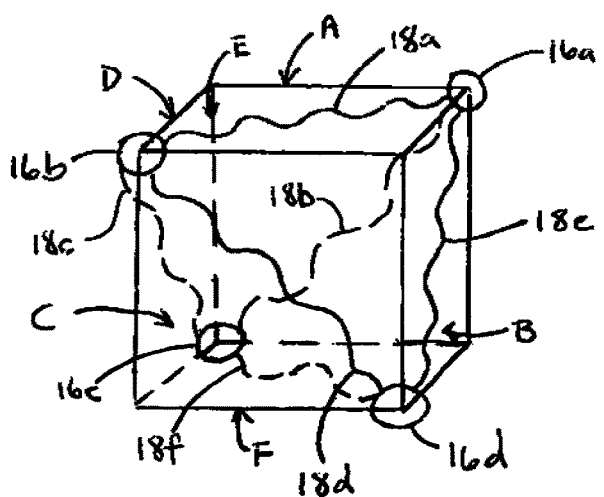

For the sake of clarity, the pins 22 indicated in FIG. 3 are shown as voids rather than pins projecting out from the mandrel 20. Also for the sake of clarity, FIGS. 5A-5C depict the mandrel 20 and the device 10 in simplistic line drawings. As will be noted, the pins 22 are not shown in FIGS. 5A-5C. In order to better show the device 10, FIGS. 5A-5C each show the same device 10 on the same mandrel 20, however the mandrel is rotated 90 degrees in each subsequent figure. More particularly, FIG. 5A shows a side A facing the viewer, and FIG. 5B, in which the mandrel 20 has been rotated 90 degrees clockwise, shows the side A to the left, obscured from the viewer. Likewise, in FIG. 5C, side A is further rotated and facing away from the viewer.

As shown in FIGS. 5A-5C, the device 10 employs four closed loop portions 16a, 16b, 16c, and 16d. The device is shown with two closed loop portions 16 on each side of the cube-like mandrel 20. The device further employs six open loop portions 18a, 18b, 18c, 18d, 18e, and 18f spanning between certain pairs of the closed loop portions 16a, 16b, 16c, and 16d. It will be noted that each of the closed loop portions 16 are directly connected to three other closed loop portions 16 by three different open loop portions 18.

It is further noted that the open loop portion 18f is not shown in FIG. 3 as the open loop portion 18f spans between closed loop portions 16c and 16d on the side F of the mandrel 20 that is obscured from the viewer. The open loop portion 18f is shown in FIGS. 4 and 5A-5C in which the mandrel 20 is not shown or shown in a transparent manner.

In certain embodiments of the present invention, the device 10 is formed on a mandrel 20 having a shape other than a three-dimensional cube-like shape. For example, the mandrel 20 may be formed in a two or three dimensional rectangular, triangular, tetrahedral, circular, oval or other regular geometric or irregular shape. It is contemplated that any number of the closed loop portions 16 and open loop portions 18 can be employed in a single device 10 of the present invention.

In certain other embodiments of the present invention, the closed loop portions 16 need not form intersection-like points for a plurality of the open loop portions 18 as shown in FIGS. 2-5C. Rather the closed loop portions 16 may be formed in a sequential manner connected to one another by the open loop portions 18, as shown in FIG. 6-8C. For example, as shown in FIG. 6, a device 90 employs only two closed loop portions 16 connected to one another by one open loop portion 18.

Figure 7B:
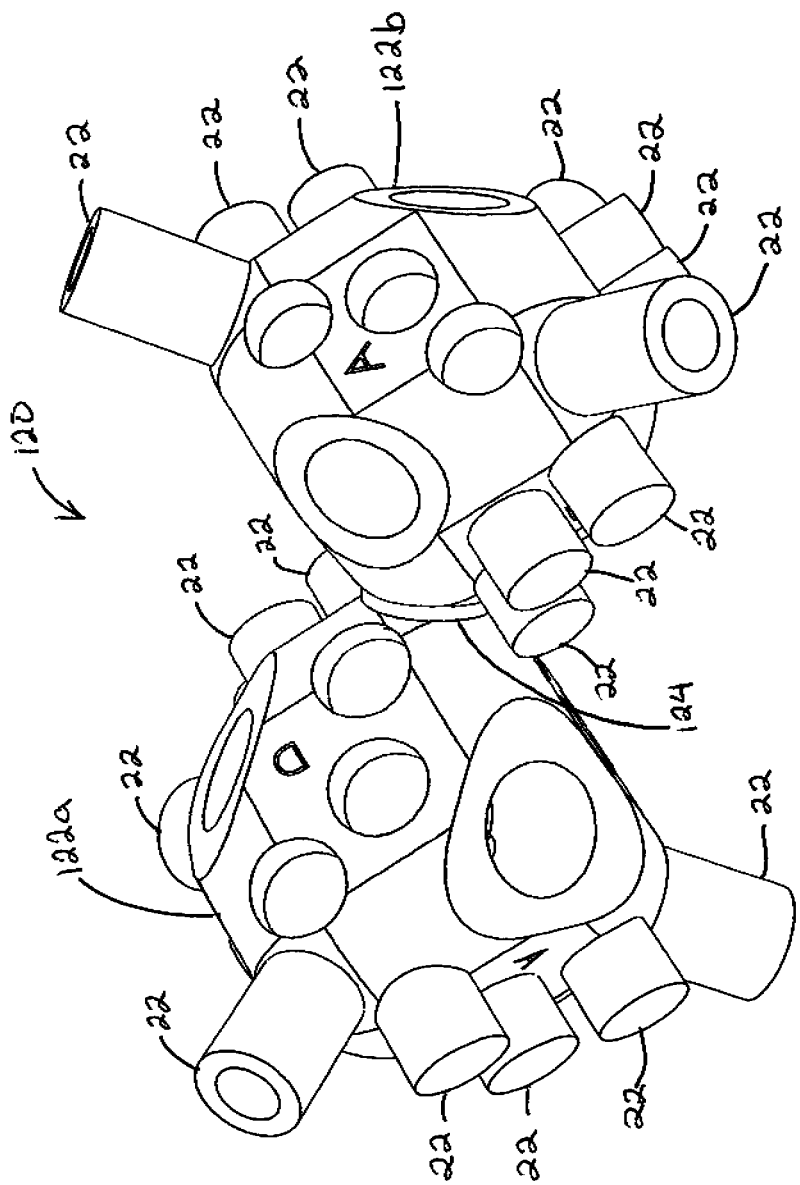
FIG. 7B is a perspective view of a mandrel employed to fabricate a device according to one embodiment of the present invention.
Figure 8A:
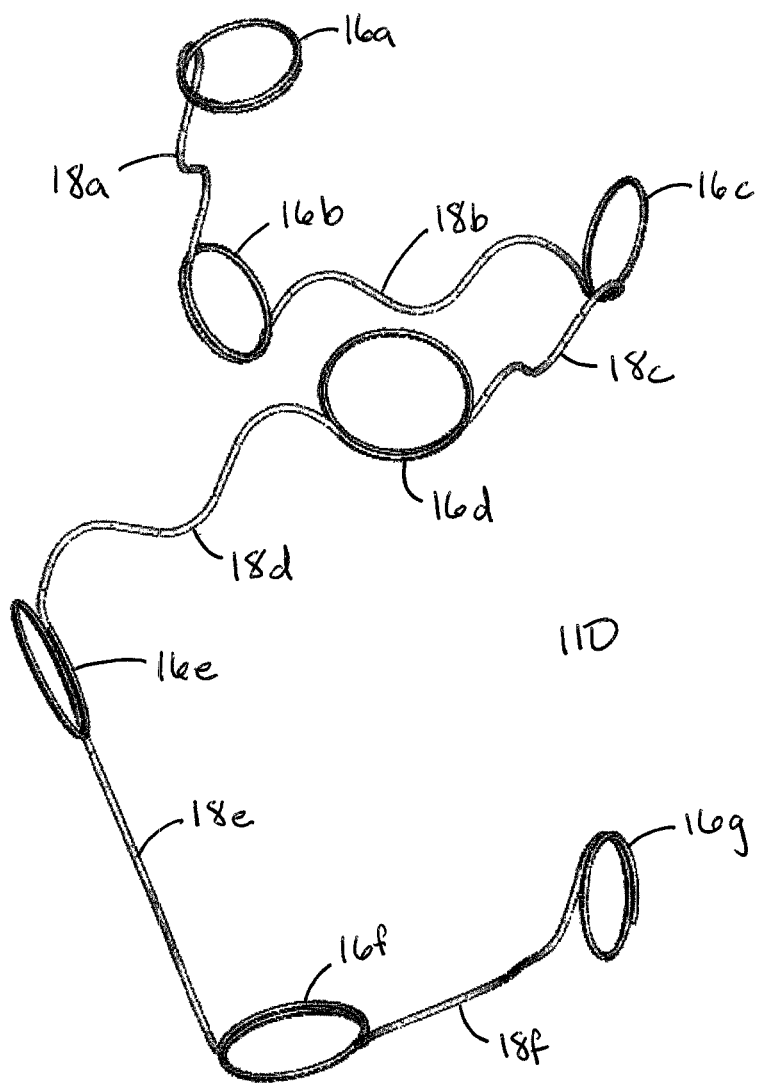
FIG. 8A is a perspective view of a device according to one embodiment of the present invention.
Figure 8B:
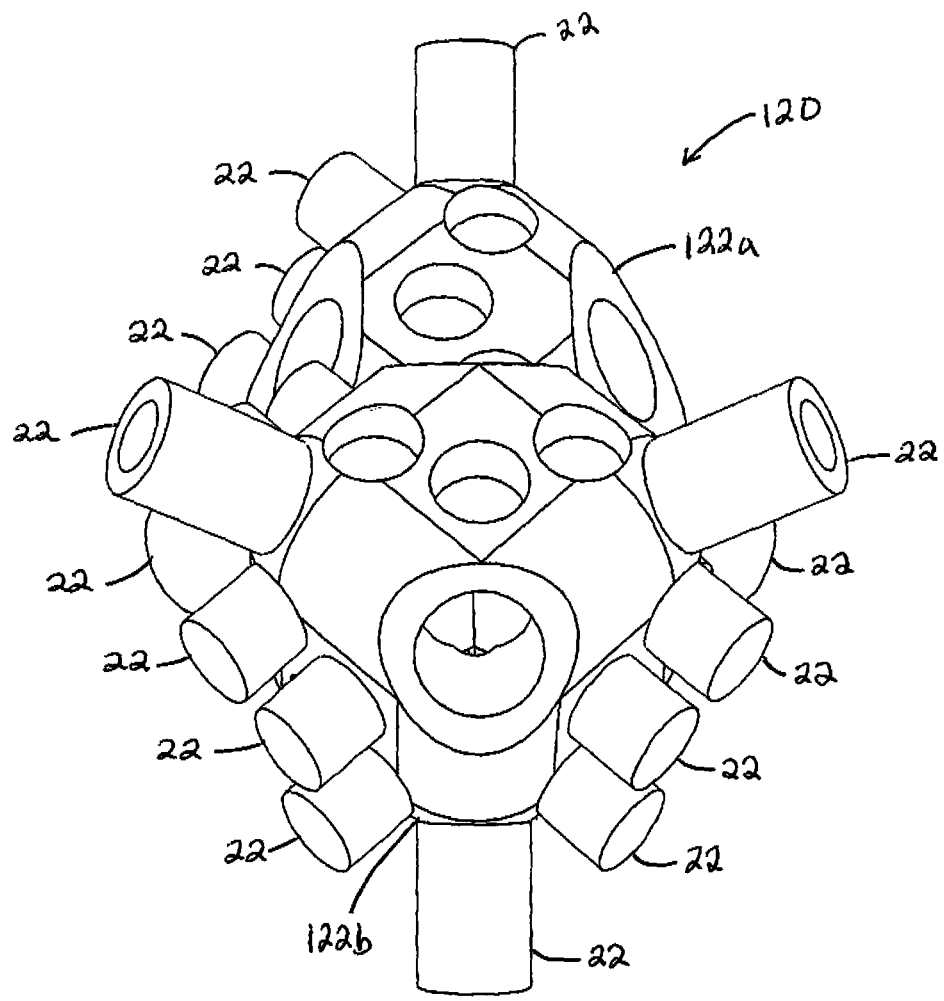
FIG. 8B is a perspective view of a mandrel employed to fabricate a device according to one embodiment of the present invention.
Figure 8C:
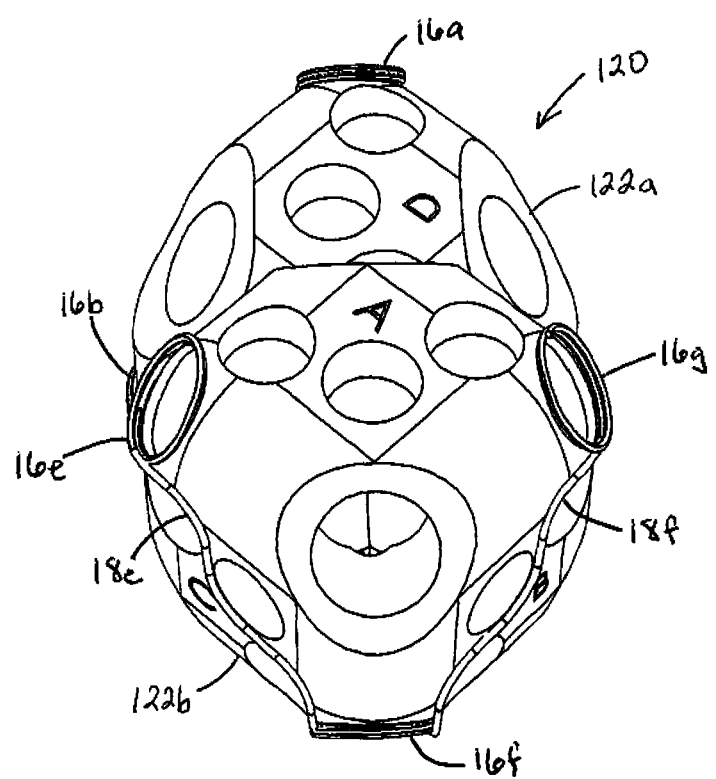
FIG. 8C is a perspective view of a device on a mandrel according to one embodiment of the present invention.

In another example, as shown in FIGS. 7A and 8A, a device 110 is shown from different perspectives in a relaxed, low-energy state as the device 110 would appear on the mandrel or fixture upon which the device 110 is formed. FIGS. 7B and 8B show a mandrel 120 used to make the device 110 from the same perspective, respectively. FIGS. 7C and 8C show the device 110 on the mandrel 120 from the same perspectives, respectively. However, for the sake of clarity, the pins 22 of the mandrel 120 have been omitted. The device 110 employs the closed loop portion 16a that is connected to the closed loop portion 16b by the open loop portion 18a. The closed loop portion 16b is, in turn, connected to the closed loop portion 16c by the open loop portion 18b. This configuration is repeated along the length of the device 110. Stated alternatively, each closed loop portion 16 is connected to the next sequentially formed closed loop portion 16 by one open loop portion 18.

As shown in FIGS. 7B and 8B, the device 110 is formed on the fixture or mandrel 120. The mandrel 120 employs pins 22 as described above regarding the device 10. The mandrel further employs one or more pins 124 that attach subassemblies 122 to one another. The pin 124 attaches a subassembly 122a to a subassembly 122b. In order to more easily relate FIGS. 7A-8C to one another, it is noted that the closed loop portion 16d is formed on the pin 124. The subassemblies 122a and 122b are formed in a generally cube-like form. However, for the sake of clarity, it is noted that the corners of the subassemblies 122a and 122b that do not employ the pin 22 or 124 have been omitted or removed from the subassemblies 122a and 122b.

It is noted that while the device 110 is shown as employing seven of the closed loop portions 16 and six of the open loop portions 18, the device 110 may employ as few as three of the closed loop portions 16 and two of the open loop portions 18. The closed loop portions 16 may have diameters ranging from approximately 2 to 20 millimeters, or 3 to 15 millimeters. The closed loop portions 16 of the device 110 may be of a uniform diameter or may vary in diameter. The number and form of the open loops employed within different open loop portions 18 may be the same or vary between different open loop portions 18 within a single device 110. For example the number of curves in a single open loop portion 18 may vary within the range of 2 to 6. The arc of the curves forming the individual open loops of the open loop portions 18 may also vary within a single open loop portion 18 or within a device 110.

In one embodiment of the present invention, the device 110 is formed by winding the microcoil 14 in the same direction for all the pins 22 on the subassembly 122a and in an opposite direction for all the pins 22 on the subassembly 122b.

In another embodiment of the present invention, the devices 210 and 310, shown in FIGS. 9 and 10 respectively, are formed on the above described mandrel 120 having the subassemblies 122a and 122b. However, as best seen through a comparison of FIG. 7A and FIGS. 9 and 10, the closed loop portion 16d of the devices 210 and 310 are formed by winding the microcoil 14 fewer rotations than the closed loop 16d of device 110. More particularly, as shown in FIG. 9, the closed loop portion 16d of the device 210 is formed by winding the microcoil 14, for example, approximately 1 to 1.25 rotations. As shown in FIG. 10, the portion of the microcoil 14 of the device 310 that is wound around what would be pin 124 of the mandrel 20 shown in FIG. 7B, is wound approximately less than one rotation. For the sake of clarity, this portion of the microcoil 14 is referenced as portion 16d' in FIG. 10. It is noted that the different degrees of rotations employed to form the closed loop 16d of device 210 and the portion 16d' of device 310 may be achieved by rotation of the subassembly 122b relative to the subassembly 122a. Accordingly, it is noted that while the number of rotations employed to form closed loop portion 16d and the portion 16d' may vary, the relative structural orientation of sequentially formed closed loop portions 16a-16d, 16a-16c to one another and the relative structural orientation of sequentially formed closed loop portions 16d-16g, 16e-16g to one another remains unchanged.

Described in Table 1 shown in FIG. 11 are various exemplary configurations of the device 310 according to the present invention. As can be seen, the device 310 may be formed of a plurality of the closed loop portions 16 having, for example, diameters ranging from 3 to 15 millimeters. The closed loop portions 18 may, for example, be formed by winding the microcoil 14 around the pin 22 from one to 2.25 rotations. The device 310 may, for example, be formed of a total of three to seven closed loop portions 16 and two to six open loop portions 18.

In another embodiment of the present invention, as shown in FIG. 12, the device 10, 110, 210, 310, in the relaxed or minimum energy state configuration, employs a series of closed loop portions 18 and open loop portions 16 that sequentially increase or decrease in size. For example, each subsequent closed loop portion 16 has a smaller diameter than the preceding closed loop portion 16 and each subsequent open loop portion 18 has a smaller height 30 and/or width 32 than the preceding open loop portion 18.

In certain embodiments of the present invention, the devices 110, 210, and 310 are formed on a mandrel 120 having a shape other than that shown in FIGS. 7B and 8B. For example, the mandrel 120 may be formed of a single or multiple two or three dimensional rectangular, triangular, tetrahedral, circular, oval or other regular geometric or irregular shape. It is contemplated that any number of the closed loop portions 16 and open loop portions 18 can be employed in a single device 110, 210, and 310 of the present invention.

In certain other embodiments of the present invention, the closed loop portions 16 may be formed proximate one another, i.e. the open loop portion 18 need not span between two of the closed loop portions 16.

In certain embodiments of the present invention, the normal planes defined by sequentially formed closed loop portions 16 and open loop portions 18 are neither coincident nor parallel to one another. In certain embodiments of the present invention, the normal planes defined by sequentially formed closed loop portions 16 intersect to form a 90 degree angle or other non-zero and non-180 degree angles. In certain embodiments of the present invention, sequentially formed open loop portions and closed loop portions form an angle greater than 90 degrees and less than 180 degrees. In certain embodiments of the present invention, the normal planes defined by certain, but not necessarily all, sequentially formed open loop portions 18 intersect to form a 90 degree angle or other non-zero and non-180 degree angle.

It is believed that the open loop portions 18 of the device 10 allow for certain improvements over known occlusion devices. For example, the relatively planar sections of the open loop portions 18 provide enhanced column strength to facilitate improved space seeking properties of the device 10. Additionally, the overall length of the open loop portions 18 allow for effective treatment of a range of target sites with a single device 10, 110. For example, a six millimeter device 10, 110, 210, 310, may be able to treat 6 to 10 millimeter aneurysms.

With respect to the closed loop portions 16 of the device 10, 110, 210, 310, the closed loop portions 16 provide intersecting point and ends to the open loop portions 18 that assist in preventing the formation of sudden or sharp angles within the device that may cause undesired pressure points within the target site.

Accordingly, the open loop portions 18 and the closed loop portions 16 function together to provide the device or packing coil 10, 110, 210, 310, according to the present invention with improved stability after deployment in a target site; improved space seeking ability within the target site; wider application for treatment of target sites of varying sizes; and increased efficacy for occlusion and treatment of the target site.

In alternative embodiments of devices according to the present invention, a device employs a combination of any of the above disclosed features.

In order to deliver the device of the present invention to a target, such as an aneurysm, the proximal end of the microcoil 14 of device is attached to the distal end of an elongate delivery device, such as a guidewire or microcatheter (not shown). The attachment may be by any of a number of ways known in the art, as exemplified by the following U.S. patents, the disclosures of which are expressly incorporated herein by reference: U.S. Pat. No. 5,108,407 to Geremia et al.; U.S. Pat. No. 5,122,136 to Guglielmi et al.; U.S. Pat. No. 5,234,437 to Sepetka; U.S. Pat. No. 5,261,916 to Engelson; U.S. Pat. No. 5,304,195 to Twyford, Jr. et al.; U.S. Pat. No. 5,312,415 to Palermo; U.S. Pat. No. 5,423,829 to Pham et al.; U.S. Pat. No. 5,522,836 to Palermo; U.S. Pat. No. 5,645,564 to Northrup et al.; U.S. Pat. No. 5,725,546 to Samson; U.S. Pat. No. 5,800,453 to Gia; U.S. Pat. No. 5,814,062 to Sepetka et al.; U.S. Pat. No. 5,911,737 to Lee et al.; U.S. Pat. No. 5,989,242 to Saadat et al.; U.S. Pat. No. 6,022,369 to Jacobsen et al.; U.S. Pat. No. 6,063,100 to Diaz et al.; U.S. Pat. No. 6,068,644 to Lulo et al.; and U.S. Pat. No. 6,102,933 to Lee et al.

Delivery of the packing coil of the present invention may be achieved by employing features of the attachment and delivery devices described in the Assignee's of the present subject matter U.S. Provisional Application Ser. No. 60/604,671, filed Aug. 25, 2004, entitled Thermal Detachment System For Implantable Devices; U.S. Provisional Application Ser. No. 60/685,342 filed May 27, 2005, entitled Thermal Detachment System For Implantable Devices; U.S. patent application Ser. No. 11/212,830 filed Aug. 25, 2005, entitled Thermal Detachment System For Implantable Devices; U.S. Provisional Application Ser. No. 60/952,520 filed Jul. 27, 2007, entitled Detachable Coil Incorporating Stretch Resistance; U.S. Provisional Application Ser. No. 61/016,154 filed Dec. 21, 2007, entitled System and Method For Locating Detachment Zone Of A Detachable Implant; and U.S. Provisional Application Ser. No. 61/324,246 filed Apr. 14, 2010, entitled Implant Delivery Device which are each herein incorporated in their entirety by reference.

A method for treating a vascular target with the device may include visualizing the target vascular site by means well-known in the art. The target vascular site may be, for example, an aneurysm branching off a parent artery. Such an aneurysm may have a dome connected to the branch artery by a neck. A catheter is passed intravascularly until it enters the dome of the aneurysm via the neck. The device is passed through the catheter with the assistance of the guidewire or microcatheter until a distal end of the device 10 enters the dome of the aneurysm.

As the device enters the aneurysm, it attempts to assume its relaxed, low-energy configuration. Because the microcoil, in its relaxed configuration, is larger than the aneurysm, it is constrained into a deployed configuration in which it tends to line the periphery of the aneurysm. In this deployed configuration, the microcoil is in an energy state that is substantially higher than its relaxed, low-energy state. Thus, when the device is deployed inside a vascular site such as an aneurysm, the confinement of the device within the site causes the device to assume a three-dimensional configuration that has a higher energy state than the relaxed energy state. Because the relaxed energy state of the device is larger (in at least one dimension) than the space in which it is deployed, the deployed device is constrained by its intimate contact with the walls of the aneurysm from returning to its minimum energy state configuration. Therefore, the device engages the surrounding aneurysm wall surface, thereby minimizing shifting or tumbling due to blood flow dynamics. Furthermore, the relaxed energy state secondary configuration (to which the device attempts to revert) is not one that is conducive to "coin stacking", thereby minimizing the degree of compaction that is experienced.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An occlusion device comprising:
   a microcoil having a relaxed configuration comprising a plurality of open loop portions interposed between a plurality of closed loop portions;
   said closed loop portions positioned in a spaced-apart orientation relative to each other;
   each open loop portion of the plurality of open loop portions formed of a plurality of waves that are each formed of curved segments alternating in opposite directions and which all define and are formed within a single, common plane; and,
   wherein at least one of said plurality of closed loops is directly connected to three of said plurality of open loop portions.

2. The occlusion device of claim 1 wherein each of the plurality of closed loop portions is positioned substantially within a different plane.

3. The occlusion device of claim 1 wherein at least two of the plurality of closed loop portions are formed by winding the microcoil in opposite directions.

4. The occlusion device of claim 1 wherein each of the plurality of closed loop portions is formed by winding the microcoil from 1 to 4 rotations.

5. The occlusion device of claim 1 wherein each open loop portion of the plurality of open loop portions is positioned substantially within a different plane relative to one another.

6. The occlusion device of claim 1 wherein an open loop portion of the plurality of open loop portions comprises from 2 to 10 individual open loops.

7. The occlusion device of claim 1 wherein sequentially formed open loop portions and closed loop portions define different non-parallel planes.

8. An occlusion device comprising:
   a microcoil having a relaxed configuration comprising a plurality of open loop portions interposed between a plurality of closed loop portions;
   said closed loop portions positioned in a spaced-apart orientation relative to each other;
   each open loop portion of the plurality of open loop portions formed substantially within a different plane relative to one another;
   each open loop portion of the plurality of open loop portions formed of a plurality of waves that alternate in opposite directions to each other and that each substantially lie within a single common plane with each other; and, at least one of said plurality of closed loop portions is directly connected to three of said plurality of open loop portions.

9. The occlusion device of claim 8 wherein at least two of the plurality of closed loop portions are formed by winding the microcoil in opposite directions.

10. The occlusion device of claim 8 wherein each of the plurality of closed loop portions is positioned substantially within a different plane.

11. The occlusion device of claim 8 wherein sequentially formed open loop portions and closed loop portions define different non-parallel planes.

12. An occlusion device comprising:
a microcoil having a relaxed configuration comprising a plurality of open loop portions and a plurality of closed loop portions;
said closed loop portions positioned in a spaced-apart orientation relative to each other;
each of the plurality of closed loop portions formed substantially within a different plane relative to one another and comprising a single closed loop;
each open loop portion of the plurality of open loop portions formed substantially within a different plane relative to one another and each open loop portion formed of a plurality of curves that alternate in opposite directions to each other and which are all substantially formed within a single, common plane; and,
wherein at least one of said plurality of closed loop portions is directly connected to three of said plurality of open loop portions.

13. The occlusion device of claim 12 wherein each of the plurality of closed loop portions is formed by winding the microcoil from 1 to 4 rotations.

14. The occlusion device of claim 12 wherein sequentially formed open loop portions and closed loop portions define different non-parallel planes.

15. The occlusion device of claim 12 wherein an open loop portion of the plurality of open loop portions is interposed between each closed loop portion of the plurality of closed loops.

* * * * *